United States Patent [19]

Bussian et al.

[11] Patent Number: 5,372,934
[45] Date of Patent: Dec. 13, 1994

[54] METHOD FOR DETERMINING LACTATE DEHYDROGENASE ISOENZYME LD1 BY STABILIZING LD1 AND INACTIVATING ISOENZYMES LD2-LD5

[75] Inventors: Ronald W. Bussian, Newark; John A. Ruglass, Middletown, both of Del.

[73] Assignee: E. I. Du Pont de Nemours and Company, Wilmington, Del.

[21] Appl. No.: 156,168

[22] Filed: Nov. 23, 1993

Related U.S. Application Data

[63] Continuation of Ser. No. 670,915, Mar. 13, 1991, abandoned.

[51] Int. Cl.$^5$ .......................... C12Q 1/32; C12Q 1/00; C12N 9/96
[52] U.S. Cl. ............................................. 435/26; 425/4; 425/188
[58] Field of Search ................................. 425/188, 20, 4

[56] References Cited

U.S. PATENT DOCUMENTS

| | | | |
|---|---|---|---|
| 3,860,484 | 1/1975 | O'Malley | 435/188 |
| 4,250,254 | 2/1981 | Modrovich | 435/188 |
| 4,250,255 | 2/1981 | Sanford | 435/26 |
| 4,891,311 | 1/1990 | Anawis et al. | 435/188 |

FOREIGN PATENT DOCUMENTS

| | | | |
|---|---|---|---|
| 0292838 | 11/1988 | European Pat. Off. | C12Q 1/32 |
| 0352547 | 1/1990 | European Pat. Off. | 435/26 |
| 9001067 | 2/1990 | WIPO | 435/26 |

OTHER PUBLICATIONS

DiSabato et al., The Jouranl of Biological Chemistry, 239:438–443 (1964).
Sanford et al., Biochemistry, 20:3207–3214 (1981).
Atha et al., The Journal of Biological Chemistry, 256: 12108–12117 (1981).
Lee et al. The Journal of Biological Chemistry, 256:625–631 (1981).
Arakawas et al. Biochemistry, 24:6756–6762 (1985).
Lee et al. Biochemistry, 26:7813–7810 (1987).

*Primary Examiner*—Douglas W. Robinson
*Assistant Examiner*—Jeffrey J. Sevigny

[57] ABSTRACT

The invention is drawn to a diagnostic assay for lactate dehydrogenase isoenzyme LD1 in a sample containing lactate dehydrogenase isoenzymes LD1–LD5. The disclosed assay involves the following steps:

(A) adding a high molecular weight polyol, preferably polyethylene glycol having a molecular weight of 8000, to the sample to stabilize isoenzyme LD1 but not isoenzymes LD2–LD5;
(B) adding an ionic amphiphile to the sample to selectively inactivate isoenzymes LD2–LD5;
(C) adding sodium lactate and NAD to the sample;
(D) determining LD1 by measuring a change in absorbance of the sample at 340 mm.

5 Claims, No Drawings

METHOD FOR DETERMINING LACTATE DEHYDROGENASE ISOENZYME LD1 BY STABILIZING LD1 AND INACTIVATING ISOENZYMES LD2-LD5

This is a continuation, of application Ser. No. 07/670.9 filed Mar. 13, 1991, now abandoned.

TECHNICAL FIELD

This invention relates to a diagnostic assay for lactate dehydrogenase isoenzyme LD1, and more specifically to a diagnostic assay for LD1 utilizing high molecular weight polyethylene glycol in an assay for LD1 in which an ionic amphiphile is used to inactivate selectively the lactate dehydrogenase isoenzymes LD2, LD3, LD4, and LD5.

background ART

Lactate dehydrogenase (LDH) is a tetrameric enzyme of two subunits, H and M, which combine to form the active LDH enzyme. Five isoenzymes, LD1, LD2, LD3, LD4, and LD5, represent the various permutations of these two subunits. The relative levels of these LDH isoenzymes, as well as the total LDH in a patient's serum, can be of importance in the diagnosis of damaged tissue. Such as damage that may result from myocardial infarction and various liver disorders.

U.S. Pat. No. 4,250,255, issued to Sanford, on Feb. 10, 1981, discloses a method for determining the activity of an isoenzyme present in a sample by assaying for the isoenzymes in the presence of a predetermined concentration of an amphiphile that has a discriminating effect on the activity of the isoenzyme, and determining the amount of isoenzyme present in the sample. In particular, this patent discloses a method for the determination of an LDH isoenzyme, such as LD1, by performing a first assay to determine total LDH activity in the sample, performing a second assay in the presence of a predetermined concentration of an ionic amphiphile that specifically inhibits the isoenzyme of interest, and determining the activity of the isoenzyme using the difference between the first and second assays. The patent does not disclose or suggest the use of polymeric polyols as a component in the assay to improve the recovery of LD1 without interfering with the selective inactivation of LD2, LD3, LD4, and LD5.

Di Sabato et al., The Journal of Biological Chemistry, 239: 438–443 (1964), disclose the dissociation of lactate dehydrogenases from chicken heart and beef heart into subunits with sodium dodecyl sulfate without marked changes in the structure of the subunits.

Sanford et al., Biochemistry, 20: 3207–3214 (1981) disclose the use of ionic surfactants, such as the anionic surfactant sodium dodecyl sulfate, to inactivate selectively LDH isoenzymes.

PCT International Patent Application publication number WO 90/01067, published Feb. 8, 1990, to Shihabi et al., discloses a reagent for inactivating LD2 through LD5 in neutral or alkaline environments which comprises the reaction product of a protein denaturing agent which works by breaking hydrogen bonds, and a thiocyanate ion.

European Patent No. 292838, published Nov. 8, 1988, to Abbott et al., discloses a method for determining LD1 isoenzyme activity of a biological fluid by preparing a reaction mixture of the biological fluid and an LDH reagent in the presence of a chaotropic agent, such as sodium perchlorate, and determining the activity of the LD1 isoenzyme. The reagent may contain a buffer, lactate, or pyruvate, and a chromogen.

The mechanism of use of polyethylene glycol (PEG) for fractional precipitation of proteins and protein crystallization is known. [Atha et al., The Journal of Biological Chemistry, 256: 12108–12117 (1981), Lee et al., The Journal of Biological Chemistry, 256: 625–631 (1981), Arakawas et al., Biochemistry, 24: 6756–6762 (1985)]. In addition, it has been shown that the presence of PEG has an effect on the thermal stability of proteins [Lee et al., Biochemistry, 26:7813–7819 (1987)]. However, none of these references suggests the effect of polyethylene glycol on improving the recovery of LD1 in an assay which uses an ionic amphiphile to selectively inactivate the LD2 through LD5 isoenzymes.

There is a need for a direct diagnostic assay for LD1 isoenzyme in automated systems utilizing an ionic amphiphile such as lithium dodecyl sulfate, to selectively inactivate the LD2 through LD5 isoenzymes, and a high molecular weight polyol to stabilize LD1 prior to its measurement.

DISCLOSURE OF THE INVENTION

The process of the present invention is for the direct measurement of lactate dehydrogenase isoenzyme LD1 in a sample of biological origin containing lactate dehydrogenase (LDH) comprises the steps of:
(A) addition of high molecular weight polymeric polyol to the sample wherein the polyol has a molecular weight of at least 1000 and two free hydroxyl groups;
(B) addition of predetermined amount of an ionic amphiphile to inactivate LD2, LD3, LD4 and LD5 in the sample; and
(C) direct determination of LD1 by measuring a change in absorbance of the sample at 340 nm.

DETAILED DESCRIPTION OF THE INVENTION

The improved assay of this invention is based on the surprising and unexpected finding that high molecular weight polymeric polyols such as polyethylene glycol (PEG), when present in a sample of biological origin, stabilizes the LD1 isoenzyme to permit its subsequent measurement without interfering with the selective inactivation or inhibition of LD2, LD3, LD4, and LD5 isoenzymes by an ionic amphiphile. Thus, the method of the present invention provides for a diagnostic assay of enhanced sensitivity for LD1 which is useful in automated systems such as the aca ® discrete clinical analyzer (a registered trademark of E. I. du Pont de Nemours and Co).

Any amphiphile that can selectively inhibit the activity of the lactate dehydrogenase isoenzymes LD2 to LD5 can be used in the assay of this invention. Amphiphile refers to an ionic compound that has a hydrophilic portion and a hydrophobic portion, and includes compounds such as surfactants. Examples of ionic amphiphiles useful in this invention include, for example, sodium dodecyl sulfate, lithium dodecyl sulfate, sodium decyl sulfate, dodecylamine hydrogen chloride, and cetylpyridinium bromide. Lithium dodecyl sulfate is preferred. The amphiphile can be chosen so that it differentially affects (specifically inhibits) the activity of the LD2 through LD5 isoenzymes, thus allowing the direct measurement of LD1.

The concentration of amphiphile can be determined readily by preparing a series of solutions covering a wide range of concentrations and determining the concentration at which maximum inactivation of the LD2 –LD5 isoenzymes occurs.

By high molecular weight polyols is meant any polymeric substance having at least two free hydroxyl-groups and having a molecular weight of at least 1000. Examples of suitable polyols for use in this invention are polysaccharides, polyethylene glycols and polypropylene glycols.

Polyethylene glycol, molecular weight of 8000, is preferred. The concentration of these polyols can be determined readily by preparing a series of solutions covering a wide range of concentrations and determining the concentration at which the measured activity of LD1 no longer increases with increasing polyol concentration while the activity of the other LD isoenzymes is maintained at a minimum level.

A preferred embodiment of the present invention is an assay for LD1 in which LD1 is determined by measurement of the change in absorbance at 340 nm and is based on the reaction of LD1 (from a solution of LDH in which LD2 –LD5 were inactivated) with sodium lactate and NAD+ to result in NADH +pyruvate +H+.

Lithium dodecyl sulfate is added to a solution of lactate dehydrogenase (LDH) so as to inactivate the LD2 through LD5 isoenzymes. The remaining LD1 catalyzes the oxidation of sodium lactate to pyruvate with simultaneous reduction of nicotinamide adenine dinucleotide (NAD) to NADH. The change in absorbance at 340 nm is directly proportional to the LD1 activity. The reaction occurs at a pH of about 8.5.

EXAMPLE 1

Stabilization of LD1 by PEG 8000 in an Assay for LD1 Using Lithium Dodecyl Sulfate A series of reaction mixtures was prepared to determine the effect of high molecular weight polyethylene glycol on the stabilization and measurement of LD1 . Stock solutions of the following were prepared: NAD (10 mg/100 µL), sodium lactate (4.4M), NAD and potassium chloride (10 mg/100 µL NAD and 0.4 mg/100 µL KCl), NAD and polyethylene glycol (10 mg/100 µL NAD and 5.26 mg/100 µL polyethylene glycol, MW 8000), NAD and mannitol (10 mg/100 µL NAD and 5.26 mg/100 µL mannitol), lithium dodecyl sulfate (LDS) in tris buffer solution (0.75M LDS in 0.1M tris, pH 8.5). Five sample reaction mixtures were prepared using the stock solutions diluted into 4.80 ml tris buffer (0.5M tris, pH 8.55 at 37° C.):

Sample 1: 50 µL sodium lactate 100 µL NAD 65 µL lithium dodecyl sulfate

Sample 2: 50 µL sodium lactate 100 µL NAD and potassium chloride 65 µL lithium dodecyl sulfate Sample 3: 50 µL sodium lactate 100 µL NAD and polyethylene glycol (MW 8000) 65 µL lithium dodecyl sulfate Sample 4: 50 µL sodium lactate 100 µL NAD and mannitol 65 µL lithium dodecyl sulfate Sample 5: 50 µL sodium lactate 32 µL NAD and KCl 32 µL NAD and polyethylene glycol (MW 8000) 32 µL NAD and mannitol 65 µL lithium dodecyl sulfate The reaction mixtures were prepared by mixing all of the reagents listed above except the LDS and sodium lactate. Two hundred µl of a standard solution of LD1, containing 300 U/L of LD1, was added to each reaction mixture. LDS and sodium lactate were then added and the activity of LD1 in each of the samples was measured in triplicates. The assays were performed using an aca ® discrete clinical analyzer and the results (average of three reactions each), calibrated to reflect concentration of the LD1 solution added to the reaction mixtures, are shown in Table 1:

TABLE 1

| Sample | LD1 (U/L) |
|---|---|
| 1 | 150 |
| 2 | 155 |
| 3 | 324 |
| 4 | 148 |
| 5 | 284 |

These results indicate that in samples containing a polyol, samples 3 and 5, the isoenzyme inactivating amphiphile LDS did not inactivate LD1 ; in other words, the polyol stabilized LD1 to permit substantially complete measurement (recovery) of the LD1 isoenzyme.

EXAMPLE 2

Selective Inactivation of LD2 By Lithium Dodecyl Sulfate in Presence of PEG 8000

A series of reaction mixtures was prepared to determine the effect of high molecular weight polyethylene glycol on the inactivation of LD2 and, under parallel conditions, of LD1 . Stock solutions of the following were prepared: NAD (10 mg/100 µL), sodium lactate (4.4M), polyethylene glycol (MW 8000, 30 mg/100 µL), lithium dodecyl sulfate (LDS) in tris buffer solution (0.75M LDS in 0.1M tris, pH 8.5). The PEG stock solution was further diluted to the concentrations shown below. Five sample reaction mixtures were prepared using the stock solutions diluted into 4.80 ml tris buffer (0.5M tris, pH 8.5 at 37° C.):

Sample 1: 50 µL sodium lactate 50 µL NAD and 50 µL of 30 mg/100 µL polyethylene glycol (MW 8000) solution 65 µL lithium dodecyl sulfate Sample 2: 50 µL sodium lactate 50 µL NAD and 50 µL of 20 mg/100 µL polyethylene glycol (MW 8000) 65 µL lithium dodecyl sulfate Sample 3: 50 µL sodium lactate 50 µL NAD and 50 µL of 10 mg/100 µL polyethylene glycol (MW 8000) 65 µL lithium dodecyl sulfate Sample 4: 50 µL sodium lactate 50 µL NAD and 50 µL of 3 mg/100 µL polyethylene glycol (MW 8000) 65 µL lithium dodecyl sulfate Sample 5: 50 µL sodium lactate 50 µL NAD and 50 µL of deionized water 65 µL lithium dodecyl sulfate The reaction mixtures were prepared by mixing all of the reagents listed above except the LDS and sodium lactate. Each of the mixtures was divided into two portions. To each of these portions was added, respectively, 200 µl of a standard solution of LD1, containing 300 U/L of LD1, and 200 µl of a standard solution of LD2, containing 250 U/L of LD2, respectively. The LDS and sodium lactate were then added to each of these portions and the activity of LD1 and LD2, respectively, in each of the samples was measured in triplicates. The assays were performed using an aca ® discrete clinical analyzer and the results (average of three reactions each), calibrated to reflect the concentrations of the LD1 solution and LD2 solution, respectively, added to the reaction mixtures, are shown in Table 2:

TABLE 2

| Sample | LD1 (U/L) | LD2 (U/L) |
|--------|-----------|-----------|
| 1 | 339 | 15 |
| 2 | 344 | 14 |
| 3 | 337 | 3 |
| 4 | 264 | 2 |
| 5 | 151 | −1 |

The results in Table 2 show polyethylene glycol stabilized LD1, the exact minimum PEG concentration necessary being dependent on the reaction milieu, but did not interfere with the selective and substantially complete inactivation of LD2 by LDS.

We claim:

1. A process for the direct measurement of lactate dehydrogenase isoenzyme LD1 in a sample of biological origin containing lactate dehydrogenase LDH comprising the steps of:
   (A) adding high molecular weight polymeric polyol to the sample wherein the polyol has a molecular weight of at least 1000 and two free hydroxyl groups;
   (B) adding a predetermined amount of an ionic amphiphile to inactivate lactate dehydrogenase isoenzymes LD2, LD3, LD4 and LD5 in the sample;
   (C) adding sodium lactate and NAD to the sample; and
   (D) determining LD1 by measuring a change in absorbance of the sample at 340 nm which is directly proportional to LD1 activity.

2. The process of claim 1 wherein the polyol is polyethylene glycol.

3. The process of claim 1 wherein the amphiphile is lithium dodecyl sulfate.

4. A process for the direct measurement of lactate dehydrogenase isoenzyme LD1 in a sample of biological origin containing lactate dehydrogenase LDH comprising the steps of:
   (A) adding high molecular weight polymeric polyol to the sample wherein the polyol has a molecular weight of at least 8000 and two free hydroxyl groups;
   (B) adding a predetermined amount of an ionic amphiphile to inactivate lactate dehydrogenase isoenzymes LD2, LD3, LD4 and LD5 in the sample;
   (C) adding sodium lactate and NAD to the sample; and
   (D) determining LD1 by measuring a change in absorbance of the sample at 340 nm which is directly proportional to LD1 activity.

5. The process of claim 2 wherein the polyethylene glycol has a molecular weight of 8000.

* * * * *